(12) United States Patent
Chen et al.

(10) Patent No.: US 11,497,411 B2
(45) Date of Patent: Nov. 15, 2022

(54) CIRCUIT APPLIED TO BIO-INFORMATION ACQUISITION SYSTEM

(71) Applicant: MEDIATEK INC., Hsin-Chu (TW)

(72) Inventors: Chih-Hsin Chen, Hsin-Chu (TW); Yu-Hung Lin, Hsin-Chu (TW)

(73) Assignee: MEDIATEK INC., Hsin-Chu (TW)

( * ) Notice: Subject to any disclaimer, the term of this patent is extended or adjusted under 35 U.S.C. 154(b) by 410 days.

(21) Appl. No.: 16/680,504

(22) Filed: Nov. 12, 2019

(65) Prior Publication Data

US 2020/0163577 A1 May 28, 2020

Related U.S. Application Data

(60) Provisional application No. 62/770,867, filed on Nov. 23, 2018.

(51) Int. Cl.
*A61B 5/053* (2021.01)
*G01N 27/02* (2006.01)

(52) U.S. Cl.
CPC ............ *A61B 5/053* (2013.01); *G01N 27/028* (2013.01); *A61B 2560/0223* (2013.01)

(58) Field of Classification Search
CPC ............ A61B 5/053; A61B 2560/0223; G01N 27/028
USPC ............................................................ 600/547
See application file for complete search history.

(56) References Cited

U.S. PATENT DOCUMENTS

| | | | |
|---|---|---|---|
| 2009/0233566 A1* | 9/2009 | Li | H04B 17/20 |
| | | | 455/226.2 |
| 2010/0121318 A1* | 5/2010 | Hancock | A61B 5/0507 |
| | | | 342/174 |
| 2011/0237904 A1 | 9/2011 | Kim | |
| 2021/0087614 A1* | 3/2021 | Hall | A61B 5/7203 |

FOREIGN PATENT DOCUMENTS

EP       3 335 631 A1    6/2018

OTHER PUBLICATIONS

Jinseok Lee, "A 255nW Ultra-High Input Impedance Analog Front-End for Non-contact ECG Monitoring", 2017 IEEE.
Mingyi Chen, "A 400GΩ input-impedance, 220mVpp linear-input-range, 2.8Vpp CM-interference-tolerant active electrode for non-contact capacitively coupled ECG acquisition", 2018 Symposium on VLSI Circuits Digest of Technical Papers.

(Continued)

*Primary Examiner* — Alex M Valvis
*Assistant Examiner* — Chanel J Jhin
(74) *Attorney, Agent, or Firm* — Winston Hsu (57) ABSTRACT

The present invention provides a circuit applied to a bio-information acquisition system, wherein the circuit includes a terminal, an output circuit, a feedback circuit and a calibration circuit. In the operations of the circuit, the terminal is arranged to receive an input signal, the output circuit is configured to generate an output signal according to the input signal, the feedback circuit is configured to receive the output signal to generate a current signal to the terminal, and the calibration circuit is configured to generate a control signal to control the feedback circuit to determine a level of the current signal according to the output signal.

11 Claims, 5 Drawing Sheets

(56) References Cited

OTHER PUBLICATIONS

Yi Zhang et al., A Novel Digitally-Controlled DC Offset Calibration Circuit for the Chopper Instrumentation Amplifier, 2018 IEEE Asia Pacific Conference on Circuits and Systems, IEEE, China, Oct. 26, 2018, pp. 38-41, XP033495681.

Qinwen Fan et al., A 1.8μ W 60 nV/√Hz Capacitively-Coupled Chopper Instrumentation Amplifier in 65 nm CMOS for Wireless Sensor Nodes, IEEE Journal of Solid-State Circuits, vol. 46, No. 7, July, IEEE, May 16, 2011, pp. 1534-1543, XP011356578.

* cited by examiner

CIRCUIT APPLIED TO BIO-INFORMATION ACQUISITION SYSTEM

CROSS REFERENCE TO RELATED APPLICATIONS

This application claims the priority of U.S. Provisional Application No. 62/770,867, filed on Nov. 23, 2018, which is included herein by reference in its entirety.

BACKGROUND

A conventional medical device generally uses large dry electrodes or wet electrodes to measure physiological signals to obtain physiological features such as bio-impedance or body fat. Recently, personal biosensors such as portable/wearable medical devices become popular for providing physiological information at all time for the reference to the user. Considering the use and design of these portable medical devices, smaller dry electrodes are more appropriate. However, smaller dry electrodes means worse electrode impedance, and quality of the signals may be worsened to influence the accuracy of the physiological information.

SUMMARY

It is therefore an objective of the present invention to provide a circuit applied to a bio-information acquisition system, which can effectively improve the signal quality to increase the accuracy of the physiological information, to solve the above-mentioned problems.

According to one embodiment of the present invention, a circuit applied to a bio-information acquisition system is provided, wherein the circuit includes a terminal, an output circuit, a feedback circuit and a calibration circuit. In the operations of the circuit, the terminal is arranged to receive an input signal, the output circuit is configured to generate an output signal according to the input signal, the feedback circuit is configured to receive the output signal to generate a current signal to the terminal, and the calibration circuit is configured to generate a control signal to control the feedback circuit to determine a level of the current signal according to the output signal.

According to another embodiment of the present invention, a circuit applied to a bio-information acquisition system is provided, wherein the circuit includes a terminal, an output circuit and a feedback circuit. In the operations of the circuit, the terminal is arranged to receive an input signal, the output circuit is configured to generate an output signal according to the input signal, and the feedback circuit is configured to compensate a phase error of the output signal generate a compensated output signal, and generate a current signal to the terminal according to the compensated output signal.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". The terms "couple" and "couples" are intended to mean either an indirect or a direct electrical connection. Thus, if a first device couples to a second device, that connection may be through a direct electrical connection, or through an indirect electrical connection via other devices and connections.

Figure 1:
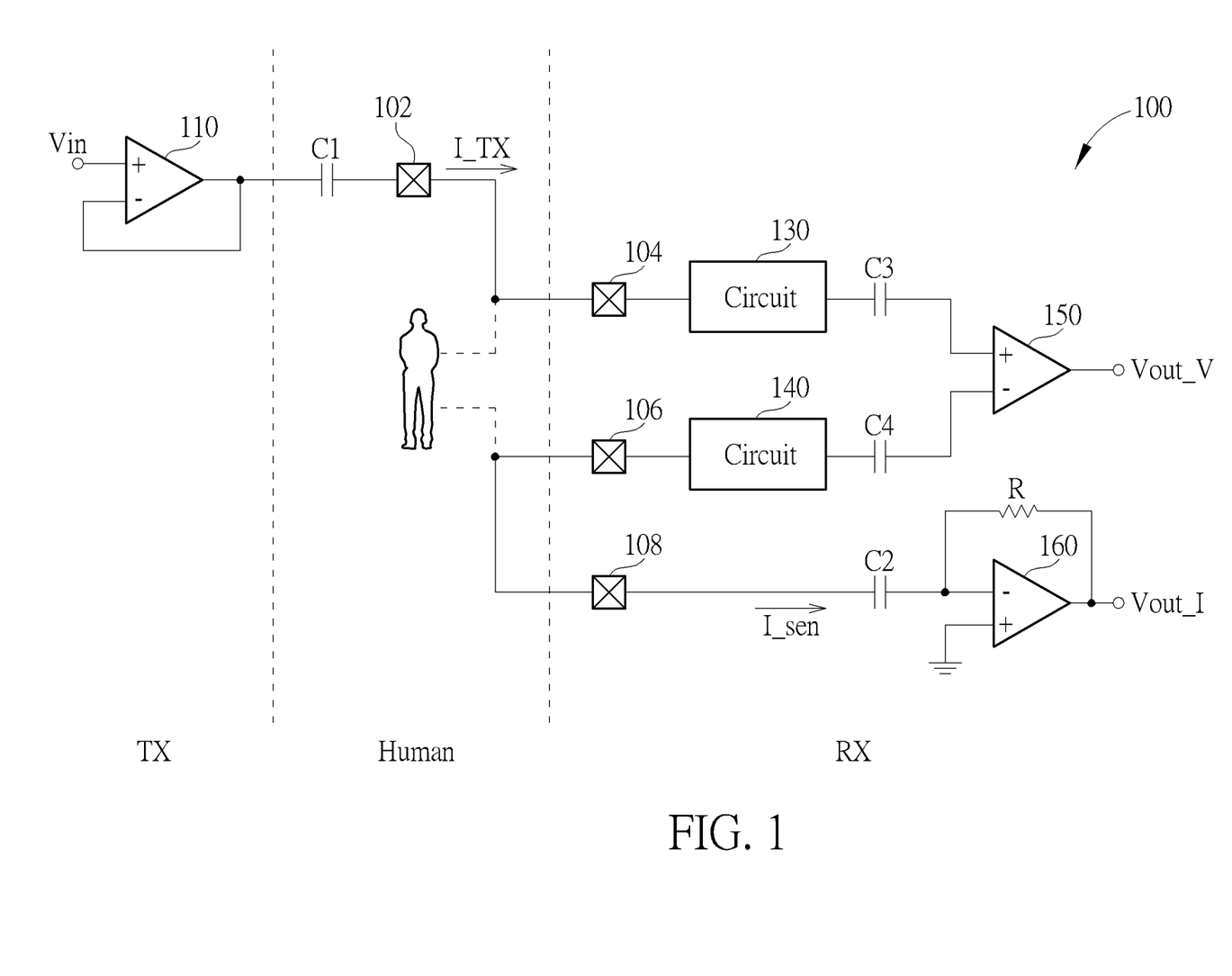
FIG. 1 is a diagram illustrating a bio-information acquisition system according to one embodiment of the present invention.

FIG. 1 is a diagram illustrating a bio-information acquisition system according to one embodiment of the present invention, wherein in this embodiment, the bio-information acquisition system is a bio-impedance acquisition system 100. As shown in FIG. 1, the bio-impedance acquisition system 100 comprises a transmitter and a receiver, wherein the transmitter comprises an output buffer 110 for outputting a transmitting signal to an electrode 102 via a capacitor C1, wherein the transmitting signal forms a current I_TX flowing into a human body. The receiver comprises three electrodes 104, 106 and 108, two circuits 130 and 140, three capacitors C2, C3 and C4, a resistor R, and two operational amplifiers 150 and 160. In this embodiment, the electrodes 102, 104, 106 and 108 are used to connect to hands and/or sole of the feet, and the bio-impedance acquisition system 100 can obtain the body voltage Vout_V and a current I_sen flowing through the human body to calculate the impedance of the human body, for example, the impedance is (Vout_V/Vout_I), wherein Vout_I represents the current I_sen flowing through the human body.

Ideally, the current I_TX outputted by the electrode 102 should be equal to the current I_sen flowing through the human body. However, because of the parasitic capacitors between the metal lines and a ground voltage of the receiver, the receiver has leakage currents flowing from the electrodes 104 and 106, and the current I_sen may be less than the current I_TX. Particularly, if the bio-impedance acquisition system 100 is built in a portable electronic device or a wearable electronic device and the electrodes 104 and 106 are small dry electrodes, the leakage currents may become larger due to the high impedance of the electrodes 104 and 106, and the accuracy of the calculated impedance is worsened due to the smaller current I_sen.

The impedance of the human body is about 500-1000 ohm, and in the body fat application, one ohm impedance error causes 0.1 body fat error. Therefore, if the allowable error of the body fat error of the medical device is 0.1%, the leakage current needs to be less than 0.1% of the current I_TX. Taking the electrode 104 whose impedance is 20 kilo-ohm as an example, the parasitic capacitance between the metal lines and the ground voltage of the receiver must be smaller than 150 femtofarad (fF). However, it's impossible to design receiver and the related printed circuit board (PCB) whose parasitic capacitance is less than 150 fF. Therefore, the inventor designs the circuit 130 between the electrode 104 and the operational amplifier 150, and designs the circuit 140 between the electrode 106 and the operational amplifier 150, to lower the leakage currents to improve the accuracy of the calculated impedance of the human body.

Figure 2:
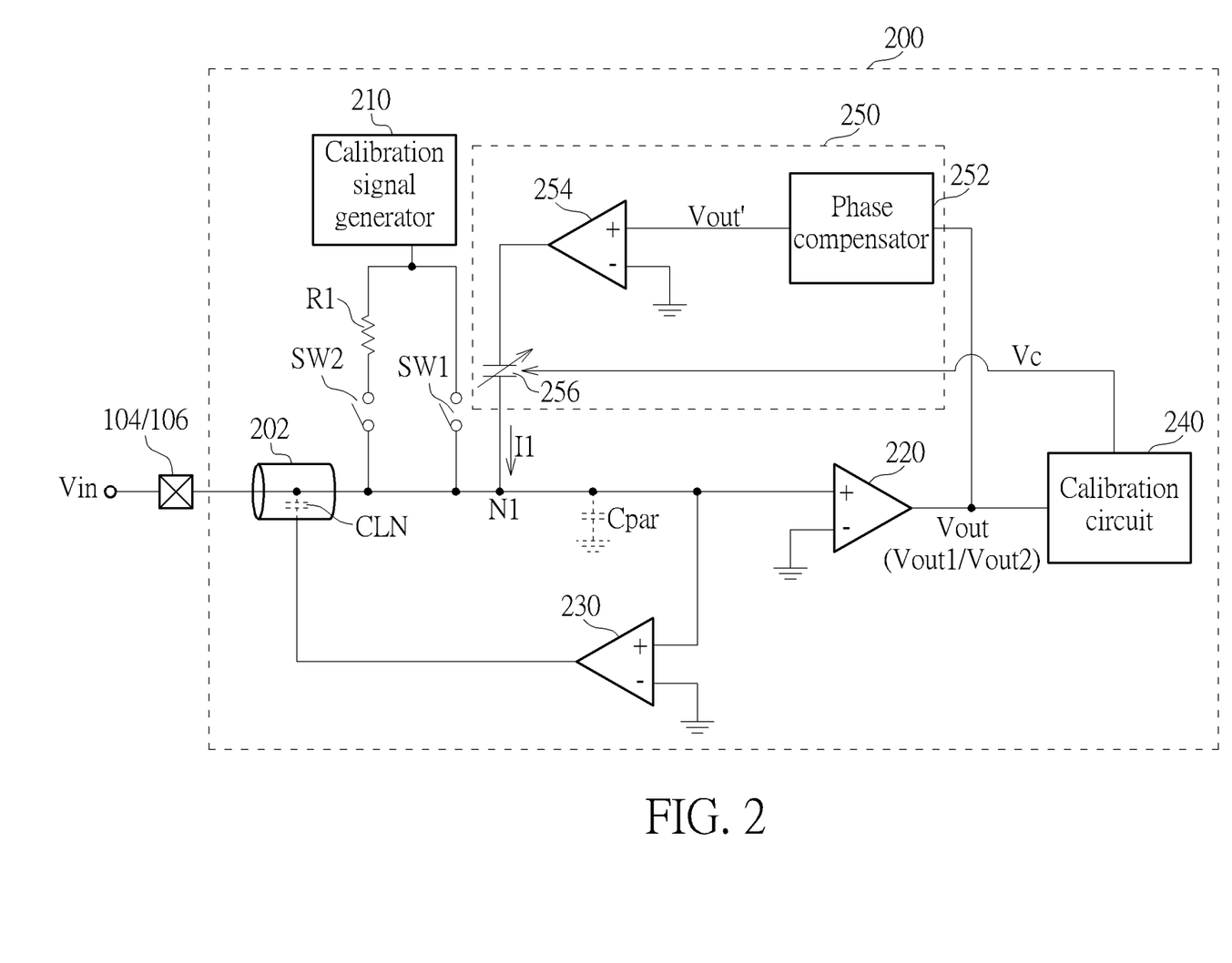
FIG. 2 is a diagram illustrating a circuit according to one embodiment of the present invention.

FIG. 2 is a diagram illustrating a circuit 200 according to one embodiment of the present invention, wherein the circuit 200 can be used to implement any one of the circuits 130 and 140. As shown in FIG. 2, the circuit 200 comprises a shield line 202, a calibration signal generator 210, an output circuit 220, a unit gain buffer 230, a calibration circuit 240, a feedback circuit 250, two switches SW1 and SW2, and a resistor R1, wherein the feedback circuit 250 comprises a phase compensator 252, an amplifier 254 and a variable capacitor 256.

In this embodiment, in order to decrease the leakage current caused by the parasitic capacitors between the ground voltage and the metal lines within the circuit 200, the shield line 202 is provided as a coarse loop to reduce most of the parasitic capacitance, and the feedback circuit 250 serves as a fine loop to reduce the remaining parasitic capacitance at the metal lines that is not implemented by the shield line. Specifically, in the operations of the circuit 200, the shield line 202 receives an input signal Vin from the electrode 104/106. The shield line has an inner conductor and an outer conductor, wherein the input signal Vin passes through the inner conductor. Then, the unit gain buffer 230 receives the input signal Vin to generate a buffered input signal to the outer conductor of the shield line 202. Therefore, because the inner conductor and the outer conductor of the shield line 202 have the same voltage level, the parasitic capacitor CLN between the inner conductor and the outer conductor of the shield line 202 becomes much smaller, and there is almost no leakage current at the inner conductor of the shield line 202. In addition, the output circuit 220 can serve as an output buffer to receive the input signal Vin to generate an output signal Vout, and the feedback circuit 250 receives the output signal Vout to generate a current signal I1 to a terminal N1 to neutralize the leakage current caused by the parasitic capacitor Cpar.

To effectively reduce the leakage current and maintain the voltage level of the input signal Vin, the current signal I1 generated by the feedback circuit 250 should be equal to the leakage current caused by the parasitic capacitor Cpar. To achieve this goal, the calibration signal generator 210 and the calibration circuit 240 are designed to control the capacitance of the variable capacitor 256 to adjust the level of the current signal I1, to neutralize the leakage current. In detail, before the bio-impedance acquisition system 100 measures the impedance of the human body, the switch SW1 is enabled and the second switch SW2 is disabled, and the calibration signal generator 210 generates a first test signal to the terminal N1 without passing through any resistor, and the output circuit 220 receives the first test signal to generate a first output signal Vout1. Then, the switch SW1 is disabled and the second switch SW2 is enabled, the calibration signal generator 210 generates a second test signal to the terminal N1 via the resistor R1, and the output circuit 220 receives the second test signal to generate a second output signal Vout2. In this embodiment, the first test signal and the second test signal are the same signal such as a sine wave, and because the resistor R1 and the parasitic capacitor Cpar form a low-pass filter to attenuate the voltage level, the first output signal Vout1 and the second output signal Vout2 have different voltage levels, and the calibration circuit 240 can refer to a difference between the first output signal Vout1 and the second output signal Vout2 to generate a control signal Vc to adjust the variable capacitor 256 to make the current signal I1 be substantially equal to the leakage current caused by the parasitic capacitor Cpar.

After the capacitance of the variable capacitor 256 is determined, the bio-impedance acquisition system 100 starts to measure the impedance of the human body, and the output signal Vout of the circuit 200 is transmitted to the capacitor C3/C4, for the operational amplifier 150 to generate the body voltage Vout_V.

Figure 3:
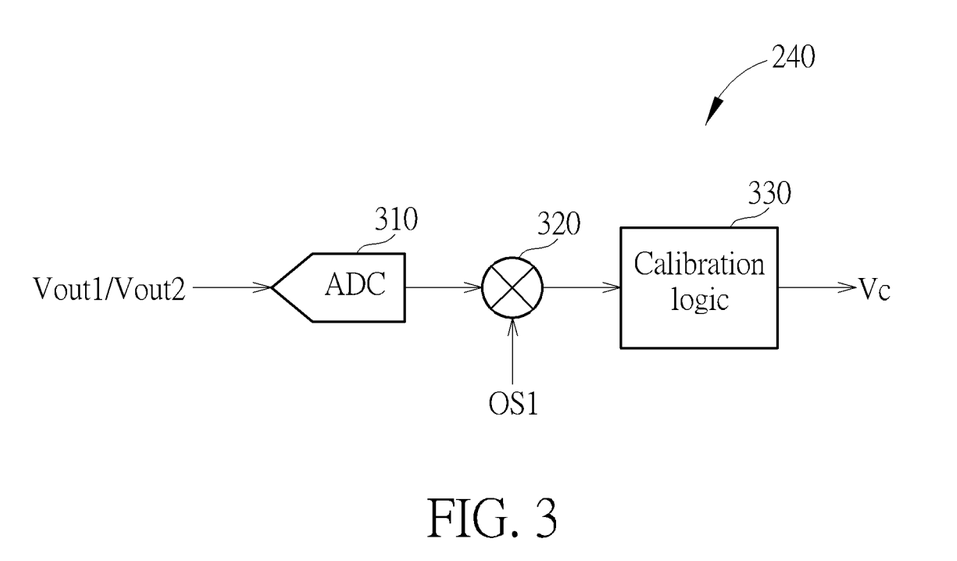
FIG. 3 is a diagram illustrating the calibration circuit according to one embodiment of the present invention.

FIG. 3 is a diagram illustrating the calibration circuit 240 according to one embodiment of the present invention. As shown in FIG. 3, the calibration circuit 240 comprises an analog-to-digital converter (ADC) 310, a mixer 320 and a calibration logic 330. In the operations of the calibration circuit 240, firstly, the ADC 310 performs analog-to-digital operation upon the first output signal Vout1 to generate a digital first output signal, and the mixer 320 mixes the digital first output signal with an oscillation signal OS1 to generate a first mixed signal. Then, the ADC 310 performs the analog-to-digital operation upon the second output signal Vout2 to generate a digital second output signal, and the mixer 320 mixes the digital second output signal with the oscillation signal OS1 to generate a second mixed signal, wherein a frequency of the oscillation signal OS1 is equal to the first test signal (or the first output signal Vout1) and the second test signal (or the second output signal Vout2). Finally, because the first mixed signal and the second mixed signal are DC signals, the calibration logic 330 can refer to the difference between the first mixed signal and the second mixed signal to estimate the capacitance of the parasitic capacitor Cpar, to generate the control signal Vc to calibrate the variable capacitor 256.

Figure 4:
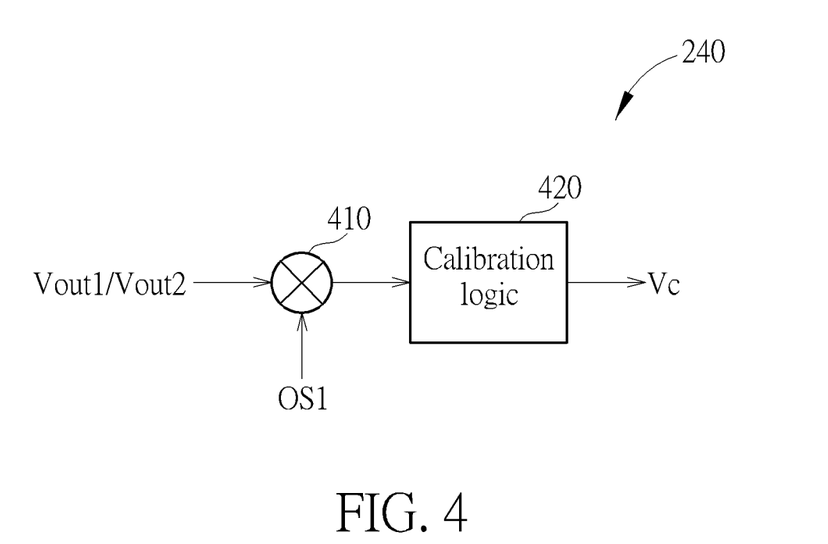
FIG. 4 is a diagram illustrating the calibration circuit according to another embodiment of the present invention.

FIG. 4 is a diagram illustrating the calibration circuit 240 according to another embodiment of the present invention. As shown in FIG. 4, the calibration circuit 240 comprises a mixer 410 and a calibration logic 420. In the operations of the calibration circuit 240, firstly, the mixer 410 mixes the first output signal Vout1 with an oscillation signal OS1 to generate a first mixed signal. Then, the mixer 410 mixes the second output signal Vout2 with the oscillation signal OS1 to generate a second mixed signal, wherein a frequency of the oscillation signal OS1 is equal to the first test signal (or the first output signal Vout1) and the second test signal (or the second output signal Vout2). Finally, because the first mixed signal and the second mixed signal are DC signals, the calibration logic 420 can refer to the difference between the first mixed signal and the second mixed signal to estimate the capacitance of the parasitic capacitor Cpar, to generate the control signal Vc to calibrate the variable capacitor 256.

In the embodiment shown in FIG. 2, the feedback circuit 250 is a positive feedback loop, and a gain of the amplifier is greater than two to successfully provide the current signal I1 to neutralize the leakage current caused by the parasitic capacitor Cpar. In the bio-impedance acquisition system 100, however, because a frequency of the input signal Vin is 50 kHz, this high frequency signal will cause the positive feedback loop unstable. Therefore, the inventor further designs the compensator 252 within the feedback circuit 250 to stabilize the positive feedback loop. Specifically, in the operations of the feedback circuit 250, the phase compensator compensates a phase error of a specific frequency (e.g. 50 kHz) of the output signal Vout to generate a compensated output signal Vout', the amplifier 254 generates an amplified signal according to the compensated output signal Vout', and the amplified signal passes through the variable capacitor 256 to generate the current signal I1 to the terminal N1. In light of above, by using the phase compensator 252 to compensate the phase error of the specific frequency 50 kHz of the output signal Vout, the phase error of the specific frequency 50 kHz may become zero, and the component corresponding to the specific frequency 50 kHz of the output signal Vout is boosting while the other components corresponding to other frequencies are attenuated. Therefore, the feedback circuit 250 will become more stable.

Figure 5:
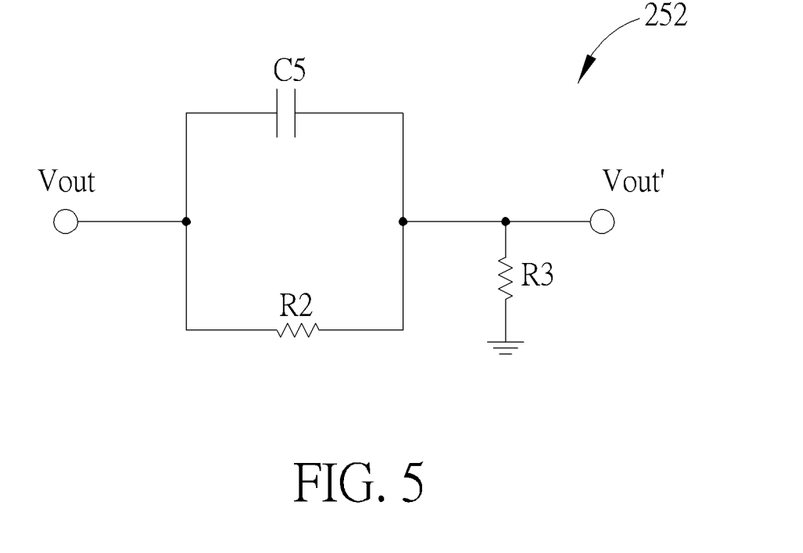
FIG. 5 is a diagram illustrating the phase compensator according to a first embodiment of the present invention.

FIG. 5 is a diagram illustrating the phase compensator 252 according to a first embodiment of the present invention. As shown in FIG. 5, the phase compensator 252 comprises two resistors R2 and R3 and a capacitor C5, wherein the resistor R2 and the capacitor C5 are connected in parallel, and the resistor R3 is coupled between resistor R2 and the ground voltage. In the phase compensator 252 shown in FIG. 5, the output signal Vout is inputted into first nodes of the resistor R2 and the capacitor C5, and the compensated output signal Vout' is generated at second nodes of the resistor R2 and the capacitor C5.

Figure 6:
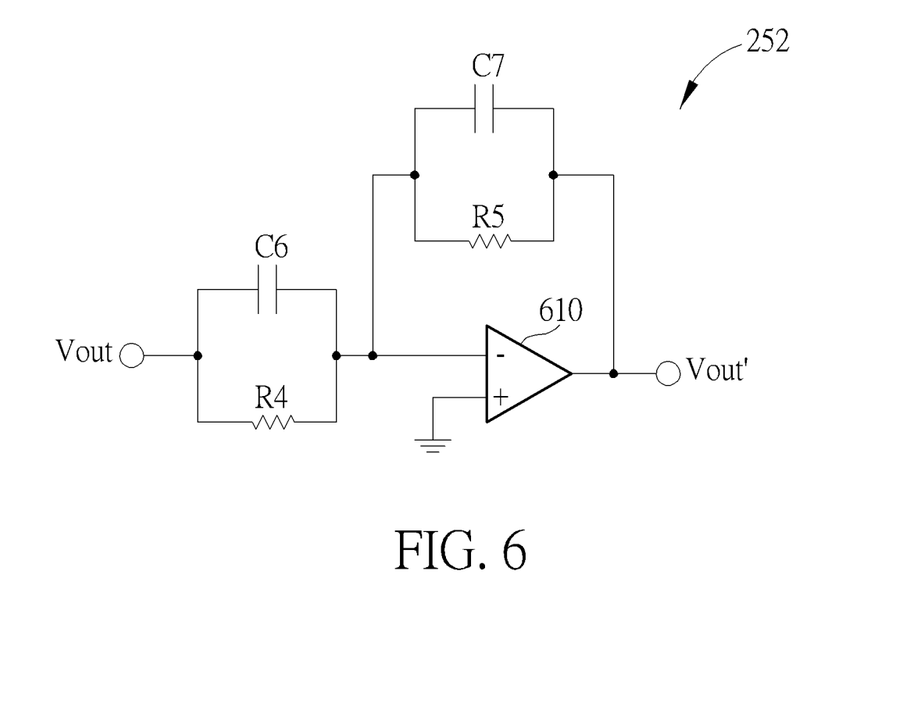
FIG. 6 is a diagram illustrating the phase compensator according to a second embodiment of the present invention.

FIG. 6 is a diagram illustrating the phase compensator 252 according to a second embodiment of the present invention. As shown in FIG. 6, the phase compensator 252 comprises two resistors R4 and R5, two capacitors C6 and C7, and an operational amplifier 610. In the phase compensator 252 shown in FIG. 6, first nodes of the resistor R4 and the capacitor C6 receive the output signal Vout, second nodes of the resistor R4 and the capacitor C6 are coupled to a negative terminal of the operational amplifier 610, first nodes of the resistor R5 and the capacitor C7 are coupled to the negative terminal of the operational amplifier 610, second nodes of the resistor R5 and the capacitor C7 are coupled to an output terminal of the operational amplifier 610, and the output terminal of the operational amplifier 610 is used to generate the compensated output signal Vout'.

Figure 7:
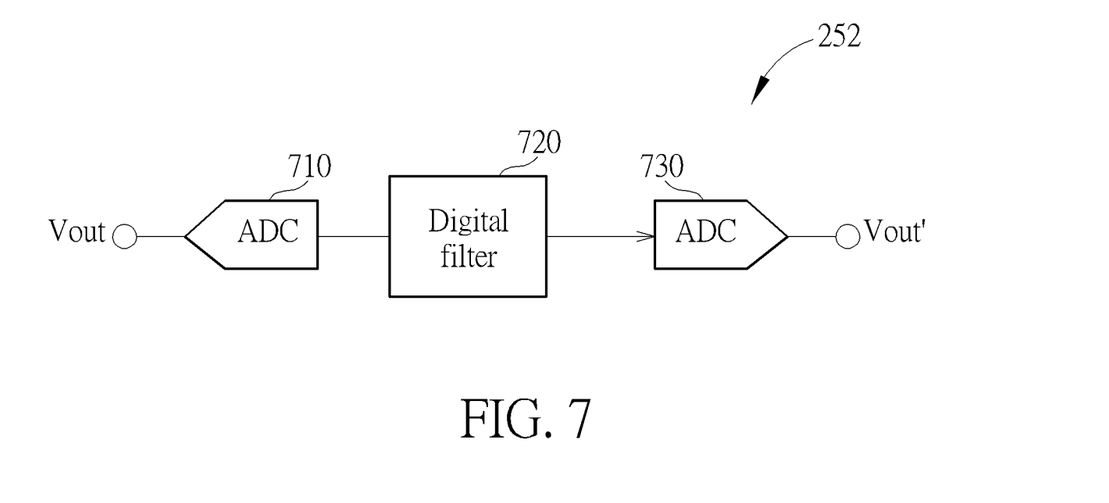
FIG. 7 is a diagram illustrating the phase compensator according to a third embodiment of the present invention.

FIG. 7 is a diagram illustrating the phase compensator 252 according to a third embodiment of the present invention. As shown in FIG. 7, the phase compensator 252 comprises an ADC 710, a digital filter 720 and a digital-to-analog converter (DAC) 730. In the operations of the phase compensator 252 shown in FIG. 7, the ADC 710 performs the analog-to-digital operation upon the output signal Vout to generate a digital output signal, the digital filter 720 filters the digital output signal to generate a filtered signal, and the DAC 730 performs the digital-to-analog operation upon the filtered signal to generate the compensated output signal Vout'.

In another embodiment of the present invention, the phase compensator 252 can be removed from the circuit 200, that is the amplifier 254 can directly receive the output signal Vout to generate the amplified signal.

In another embodiment, the calibration signal generator 210, the switches SW1 and SW2, the resistor R1 and the calibration circuit 240 can be removed from the circuit 200, that is the variable capacitor 256 can be replaced by a capacitor whose capacitance is pre-determined.

Briefly summarized, in the circuit applied to the bio-information acquisition system of the present invention, the calibration circuit is designed to adjust the level of the current signal to neutralize the leakage current to increase the accuracy of the calculation of the impedance of the human body. In addition, the phase compensator is designed to compensate the specific frequency (e.g. 50 kHz) in the feedback circuit to stabilize the positive feedback loop.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A circuit applied to a bio-information acquisition system, comprising:
    a terminal, for receiving an input signal;
    an output circuit, for generating an output signal according to the input signal;
    a feedback circuit, for receiving the output signal to generate a current signal to the terminal;
    a calibration circuit, coupled to the output circuit and the feedback circuit, for generating a control signal to control the feedback circuit to determine a level of the current signal according to the output signal; and
    a calibration signal generator, for generating a plurality test signals to the terminal to serve as a plurality of input signals;
    wherein the output circuit receives the plurality of input signals to generate a plurality of output signals, and the calibration circuit generates the control signal to control the feedback circuit to determine the level of the current signal according to the plurality of output signal;
    wherein the plurality of test signals comprises a first test signal and a second test signal, and the calibration signal generator generates the first test signal to the terminal without passing through any resistor, and the output circuit receives the first test signal to generate a first output signal; and the calibration signal generator generates the second test signal to the terminal through a resistor, and the output circuit receives the second test signal to generate a second output signal; and the calibration circuit generates the control signal to control the feedback circuit to determine the level of the current signal according to the first output signal and the second output signal.

2. The circuit of claim 1, wherein the calibration circuit controls the feedback circuit to determine the level of the current signal, to make the feedback circuit generate the current signal to the terminal to neutralize a leakage current at the terminal.

3. The circuit of claim 1, wherein the calibration circuit controls the feedback circuit to determine the level of the current signal to make the input signal not be attenuated due to a leakage current at the terminal.

4. The circuit of claim 1, wherein the calibration circuit comprises:
    a mixer, for mixing the first output signal with an oscillation signal to generate a first mixed signal, and further mixing the second output signal with the oscillation signal to generate a second mixed signal; and
    a calibration logic, coupled to the mixer, for generating the control signal according to a difference between the first mixed signal and the second mixed signal.

5. The circuit of claim 4, wherein a frequency of the oscillation signal is equal to a frequency of the first test signal and the second test signal.

6. The circuit of claim 1, wherein the feedback circuit comprises:
    an amplifier, coupled to an output terminal of the output circuit, for generating an amplified signal according to the output signal; and a variable capacitor, coupled between an output terminal of the amplifier and the terminal of the circuit;

wherein the calibration circuit generates the control signal to control the variable capacitor to determine the level of the current signal according to the output signal.

7. The circuit of claim 6, wherein the feedback circuit is a positive feedback loop, and a gain of the amplifier is greater than two.

8. The circuit of claim 6, wherein the feedback circuit further comprises:

a phase compensator, for compensating a phase error of the output signal to generate a compensated output signal;

wherein the amplifier generates the amplified signal according to the compensated output signal.

9. The circuit of claim 8, wherein the phase compensator compensates the phase error and boosts a gain of a specific frequency of the output signal to generate the compensated output signal.

10. The circuit of claim 9, wherein the specific frequency is 50 kHz.

11. The circuit of claim 1, wherein the bio-information acquisition system is a bio-impedance acquisition system.

* * * * *